United States Patent [19]

Giller et al.

[11] 3,947,444

[45] Mar. 30, 1976

[54] PROCESS FOR PRODUCING N₁-(DIHYDROXYALKYL)-5-SUBSTITUTED URACILS

[76] Inventors: Solomon Aronovich Giller, ulitsa Pernavas, 10, kv. 76; Regina Abramovna Zhuk, ulitsa Gorkogo, 77, kv. 20; Anna Eduardovna Berzinya, ulitsa Raunas 35/2, kv. 29; Laima Avgustovna Sherinya, ulitsa Rainas, 43, kv. 43, all of Riga, U.S.S.R.

[22] Filed: June 21, 1973

[21] Appl. No.: 372,419

[52] U.S. Cl. .............................................. 260/260
[51] Int. Cl.² ................................. C07D 239/54
[58] Field of Search ................................... 260/260

[56] References Cited

OTHER PUBLICATIONS

Houben–Weyl, Methoden der Organischen Chemie, 1963, Band VI/2, pp. 763–766.
Chemical Abstracts, Vol. 55, 1961, 16433b.
Gaylord, Reduction with Complex Metal Hydrides, Interscience Publishers Inc., N.Y., 1956, pp. 593, 594, 634, 635, & 760.

*Primary Examiner*—Richard J. Gallagher
*Assistant Examiner*—Anne Marie T. Tighe
*Attorney, Agent, or Firm*—Haseltine, Lake & Waters

[57] ABSTRACT

A process for producing N₁-(dihydroxyalkyl)-5-substituted uracils of the formula:

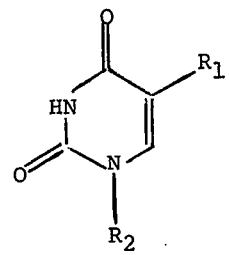

wherein
R₁ is hydrogen, methyl, a trihalomethyl, a halogen,
R₂ is 1,4-dihydroxybutyl-2,1,4-dihydroxypentyl-2,2,5-dihydroxypentyl-1,
characterized by reducing N₁-(butyrolactone)uracils of the formula:

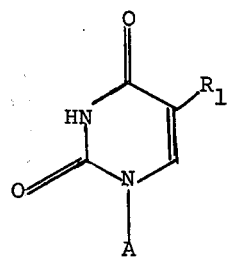

wherein
R₁ is hydrogen, methyl, a trihalomethyl, a halogen,
A is:

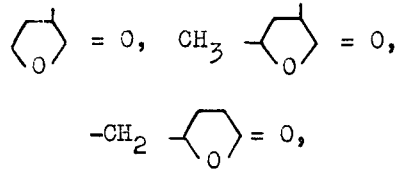

with an alkali metal boron hydride in an aqueous or aquo-alcoholic solution at a temperature ranging from 15° to 50°C.

5 Claims, No Drawings

PROCESS FOR PRODUCING N₁-(DIHYDROXYALKYL)-5-SUBSTITUTED URACILS

The present invention relates to a process for producing nucleoside analogues and, more specifically, to a process for producing $N_1$-(dihydroxyalkyl)-5-substituted uracils corresponding to the generic formula:

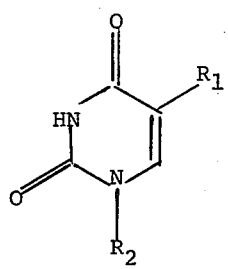

wherein
$R_1$ is hydrogen, methyl, a trihalomethyl or a halogen;
$R_2$ is 1,4-dihydroxybutyl-2, 1,4-dihydroxypentyl-2, 2,5-dihydroxypentyl-1.

Said compounds are analogues of pyrimidine-nucleosides, wherein a sugar residue is replaced by a dihydroxyalkyl group. Such compounds are particularly interesting as possible inhibitors of nucleic exchange and may be useful for the production of analogues of mono-, oligo-nucleotides and nucleic acids.

Known in the art is a process for producing $N_1$-(2,3-dihydroxypropyl-1)-uracil by alkylation of uracil or 4-ethoxy-2-keto-1,2-dihydropyrimidine with glycidol in a dimethylformamide medium in the presence of anhydrous potassium carbonate (cf. N. Ueda, T. Kawabata, K. Takemoto, L. Heterocyclic Chem., 1971, 8, 827).

Also known in the art is a process for producing $N_1$-(3',5'-dihydroxypentyl-1)-uracil (cf. B. R. Baker, T. J. Shawan, J. Med. Chem., 1966, 9, 73) by condensing uracil with 1-chloro-3,5-diacetoxypentane, followed by hydrolysis of acetyl groups with butylamine.

None of said prior-art processes can be applied for the synthesis of other $N_1$-dihydroxyalkyluracils.

It is an object of the present invention to provide a process for producing $N_1$-(dihydroxyalkyl)-5-substituted uracil derivatives which would enable the production of all the compounds corresponding to the generic formula given hereinabove.

This object is accomplished by the process for producing $N_1$-(dihydroxyalkyl)-5-substituted uracils of the formula:

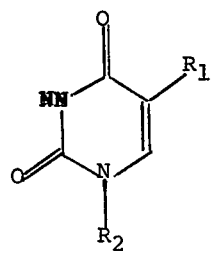

wherein
$R_1$ is hydrogen, methyl, a trihalomethyl or a halogen,
$R_2$ is 1,4-hydroxybutyl-2, 1,4-dihydroxypentyl-2, 2,5-dihydroxypentyl-1,
which, according to the present invention, comprises reducing $N_1$-(butyrolactone)uracils of the formula:

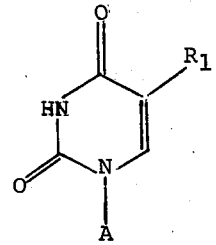

wherein $R_1$ is hydrogen, methyl, a trihalomethyl or a halogen, and A is

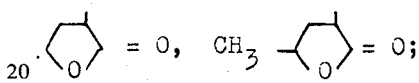

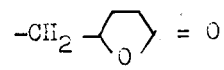

with an alkali metal boron hydride in an aqueous or aquo-alcoholic solution at a temperature ranging from 15° to 50°C. The reaction of interaction of the components proceeds according to schemes I, II, III:

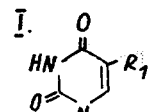

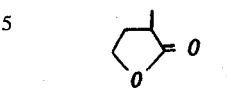

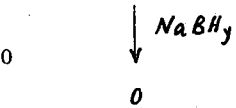

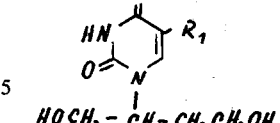

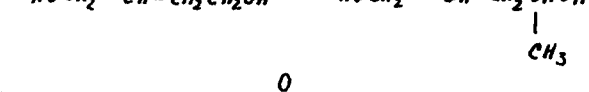

The process for producing said $N_1$-(dihydroxyalkyl)-uracils is performed in the following manner.

A suspension of a $N_1$-(butyrolactone)-5-substituted uracil in water is gradually added, with stirring, to an aqueous or alcoholic solution of an alkali metal boron hydride such as sodium boron hydride at room temperature. 20–30 minutes after the addition of the total amount of the $N_1$-(butyrolactone)-uracil, its complete dissolution in the reaction mixture is observed.

The reaction mixture is allowed to stand for 2–3 hours, whereafter it is acidified with acetic acid to pH = 5 decompose the excess of said boron hydride, passed through a column filled with a cationite "Amberlite-IR-120", and eluted with water. The eluate is passed through a column with an anionite "Dowex-3", eluted with water and then with a 0.5N aqueous ammonia solution.

The aqueous eluate, after evaporation, gives $N_1$-(dihydroxyalkyl)-5-substituted uracil derivatives. The ammoniacal liquor contains a by-product of the reaction, viz. an ammonium salt of a corresponding hydroxy-acid.

For better understanding of the present invention, the following Examples illustrating the production of $N_1$-(dihydroxyalkyl)-5-substituted uracil derivatives are given hereinbelow.

EXAMPLE 1: PRODUCTION OF $N_1$-(1,4-DIHYDROXYBUTYL-2)-URACIL

To a solution of 0.8 g (0.022 mol) of sodium boron hydride in 40 ml of water there is added, under stirring, a suspension of 3 g (0.015 mol) of $N_1$-($\alpha$-butyrolactone)uracil in 40 ml of water. The reaction mixture is stirred for 2–3 hours at room temperature. Then, the excess sodium boron hydride is decomposed with acetic acid, passed through a column with a cationite such as "Amberlite IR-120", and eluted with water. The eluate is passed through a column with "Dowex-3" anionite, eluted with water and then with a 0.5M ammonia solution. After evaporation, the aqueous eluate gives 1.7 g (57% of the theoretical amount) of $N_1$-(1,4-dihydroxybutyl-2)uracil in the form of white crystals which are then recrystallized from ethanol. Melting point 108°–110°C.

UV-spectrum, pH = 2, $\lambda_{max}266(\epsilon 9.630)$; pH =12$\lambda_{max}265(\epsilon 7.100)$;

IR-spectrum 1,060 cm$^{-1}$ ($\nu_{C\text{-}OH}$), 3,300–3,450 cm$^{-1}$; ($\nu_{OH}$) 1,680, 1,720 cm$^{-1}$ ($\nu_{CO}$).

Analysis. Found, %: C, 48.25; H, 6.20; N, 14.12. $C_8H_{12}N_2O_4$. Calculated, %: C, 47.99; H, 6.04; N, 13.99.

EXAMPLE 2: PRODUCTION OF $N_1$-(1,4-DIHYDROXYBUTYL-2)-5-FLUOROURACIL

The reaction is conducted as described in Example 1. Using 3 g (0.014 mol) of $N_1$-($\alpha$-butyrolactone)-5-fluorouracil and 0.8 g (0.022 mol) of sodium boron hydride, there is obtained 1 g (33% of the theoretical amount) of $N_1$-(1,4-dihydroxybutyl-2)-5-fluorouracil in the form of a white crystalline substance. The desired product is recrystallized from ethanol. Melting point 181°–182°C.

UV-spectrum pH = 2$\lambda_{max}276(\epsilon 8,540)$, pH = 12$\lambda_{max}276(\epsilon 6,420)$ IR-spectrum 1,670; 1,720 cm$^{-1}$ ($\nu_{CO}$), 3,200–3,400 ($\nu_{OH}$), 1,050 ($\nu_{C\text{-}OH}$).

Analysis. Found, %: C, 44.49; H, 5.10; N, 12.93; F, 8.16. $C_8H_{11}N_2O_4F$. Calculated, %: C, 44.04; H, 5.08; N, 12.84; F, 8.70.

EXAMPLE 3: PRODUCTION OF $N_1$-(1,4-DIHYDROXYPENTYL-2)-5-METHYLURACIL

The reaction is conducted as described in Example 1. Using 3.3 g (0.015 mol) of $N_1$-($\gamma$-methyl-$\alpha$-butyrolactone)-5-methyluracil and 0.8 g (0.022 mol) of sodium boron hydride, there is obtained 1.2 g (53% of the theoretical amount) of $N_1$-(1,4-dihydroxypentyl-2)-5-methyluracil which is then recrystallized from ethanol. Melting point 166°–168°C.

UV-spectrum pH = 2$\lambda_{max}273(\epsilon 9.200)$, pH = 12$\lambda_{max}273(\epsilon 7,100)$.

IR-spectrum 1,680; 1,700 cm$^{-1}$ ($\nu_{CO}$); 3,230–3,420 cm$^{-1}$ ($\nu_{OH}$); 1,050 cm$^{-1}$ ($\nu_{C\text{-}OH}$).

Analysis. Found, %: C, 52.05; H, 7.28; N, 12.42. $C_{10}H_{16}N_2O_4$. Calculated, %: C, 52.19; H, 7.02; N, 12.28.

EXAMPLE 4: PRODUCTION OF $N_1$-(2,5-DIHYDROXYPENTYL-1)-5-TRIFLUOROMETHYLURACIL

The reaction is conducted as described in Example 1. Using 4.2 g (0.015 mol) of $N_1$-(butyrolactone-$\gamma$-methylene)-5-trifluoromethyluracil and 0.8 g (0.022 mol) of sodium boron hydride, there is obtained 0.8 g (28% of the theoretical amount) of $N_1$-(2,5-dihydroxypentyl-1)-5-trifluoromethyluracil. The product is recrystallized from ethanol. Melting point is 195°–197°C.

UV-spectrum pH = 2 $\lambda_{max}262(\epsilon 9.940)$ pH = 12$\lambda_{max}261(\epsilon 6.720)$;

IR-spectrum 1,680; 1,700 cm$^{-1}$ ($\nu_{CO}$); 3,200–3,400 cm$^{-1}$ ($\nu_{OH}$), 1,050; 1,090 cm$^{-1}$ ($\nu_{C\text{-}OH}$).

Analysis. Found, %: C, 42.85; H, 4.60; N, 9.99; F, 19.73. $C_{10}H_{13}N_2O_4F_3$. Calculated, %: C, 42.55; H, 4.64; N, 9.79; F, 20.20.

1. A process for producing $N_1$-(dihydroxyalkyl)-5-substituted uracils of the formula:

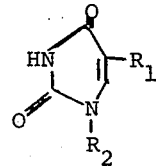

where $R_1$ is selected from the group consisting of hydrogen, methyl, trifluoromethyl and fluorine; $R_2$ is selected from the group consisting of 1,4-dihydroxybutyl-2, 1,4-dihydroxypentyl-2, and 2,5-dihydroxypentyl-1, comprising reducing $N_1$-(butyrolactone) uracils of the formula:

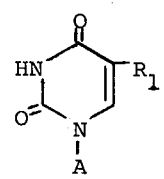

wherein $R_1$ is selected from the group consisting of hydrogen, methyl, trifluoromethyl and fluorine; and A is selected from the group consisting of

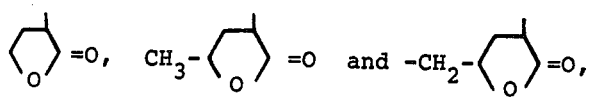

with an alkali metal boron hydride in an aqueous or aqua-alcoholic solution at a temperature ranging from 15° to 50°C.

2. A process according to claim 1 wherein $R_1$ is hydrogen and A is

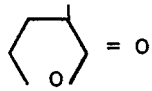

3. A process according to claim 1 wherein $R_1$ is fluorine and A is

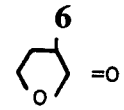

4. A process according to claim 1 wherein $R_1$ is methyl, and A is

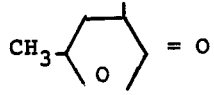

5. A process according to claim 1 wherein $R_1$ is trifluoromethyl and A is

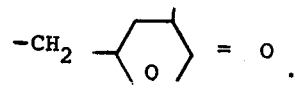

* * * * *